United States Patent [19]

Singer

[11] Patent Number: 5,711,308
[45] Date of Patent: Jan. 27, 1998

[54] WEARABLE APPARATUS FOR MEASURING DISPLACEMENT OF AN IN VIVO TYMPANUM AND METHODS AND SYSTEMS FOR USE THEREWITH

[75] Inventor: Andrew J. Singer, Palo Alto, Calif.

[73] Assignee: Interval Research Corporation, Palo Alto, Calif.

[21] Appl. No.: 475,349

[22] Filed: Jun. 7, 1995

[51] Int. Cl.$^6$ .................................................. A61B 5/12
[52] U.S. Cl. .................................................. 128/746
[58] Field of Search .......................... 128/746, 774; 73/585

[56] References Cited

U.S. PATENT DOCUMENTS

| | | | |
|---|---|---|---|
| 4,374,526 | 2/1983 | Kemp | 128/746 |
| 4,413,634 | 11/1983 | Marchbanks | 128/746 |
| 4,834,111 | 5/1989 | Khanna et al. | 128/774 |
| 4,841,986 | 6/1989 | Marchbanks | 128/746 |
| 5,018,203 | 5/1991 | Sawyers et al. | 381/71 |
| 5,083,312 | 1/1992 | Newton et al. | 381/68.4 |
| 5,105,822 | 4/1992 | Stevens et al. | 128/746 |
| 5,452,359 | 9/1995 | Inanega et al. | 81/25 |

OTHER PUBLICATIONS

Zhou, Bintz, Anderson & Bright, "A Life-Sized Physical Model of the Human Cochlea with Optical Holographc Readout", J. Acoust. Soc. Am. 93(3), Mar. 1993, pp. 1517–1523.

Hellbaum, Gunther, Clause, Murphy, "High-Temperature Microphone with Fiber-Optic Output," Laser Tech Briefs Fall, 1994, pp. 45–46.

*Primary Examiner*—Max Hindenburg
*Attorney, Agent, or Firm*—Brooks & Kushman

[57] ABSTRACT

Methods and systems for sensing an auditory environment using a tympanic membrane of an individual are disclosed. An embodiment of a method comprises a step of dynamically sensing a displacement of the tympanic membrane in response to excitation by the auditory environment. An electrical signal based upon the sensed displacement is produced. Consequently, the electrical signal is representative of the auditory environment as sensed by the individual. Embodiments for sensing the displacement of the tympanic membrane are based upon laser interferometry and ultrasonic ranging. Further disclosed are methods and systems for modifying a sensed auditory environment, and methods and systems for producing a virtual auditory environment based upon directly sensing the displacement of the tympanic membrane of an individual.

64 Claims, 7 Drawing Sheets

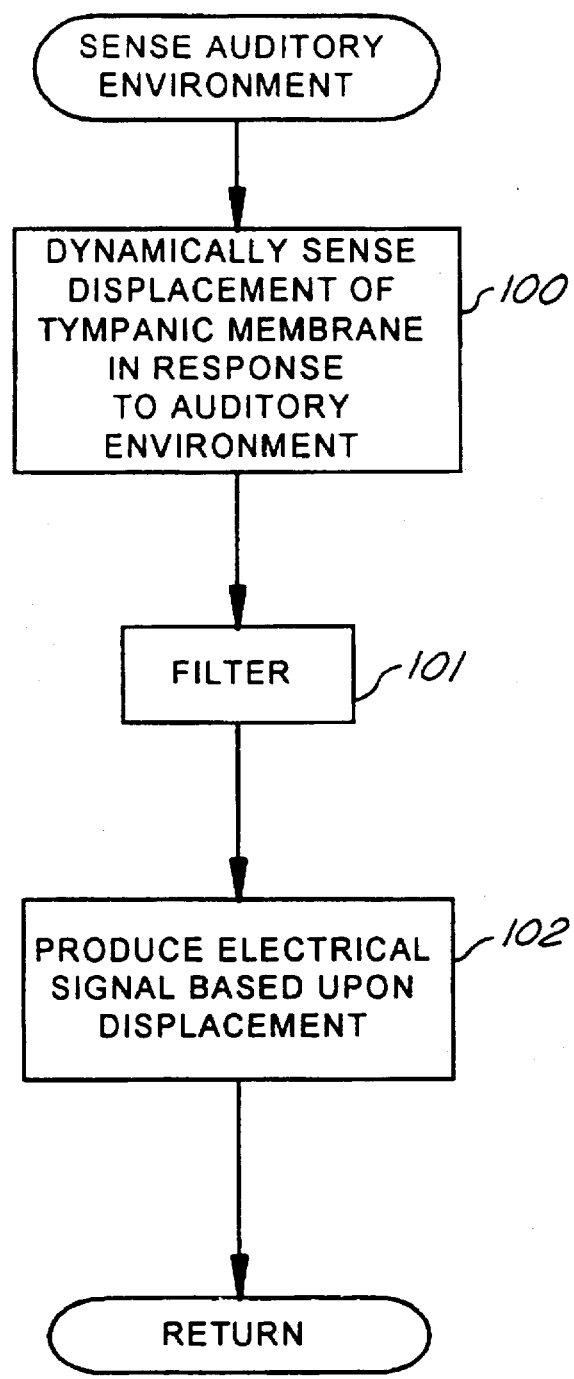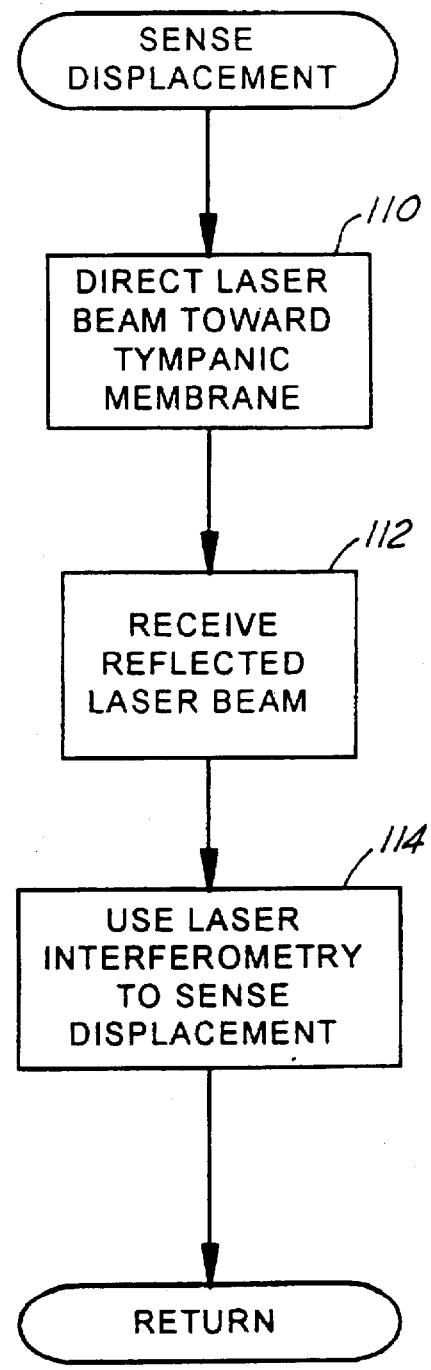

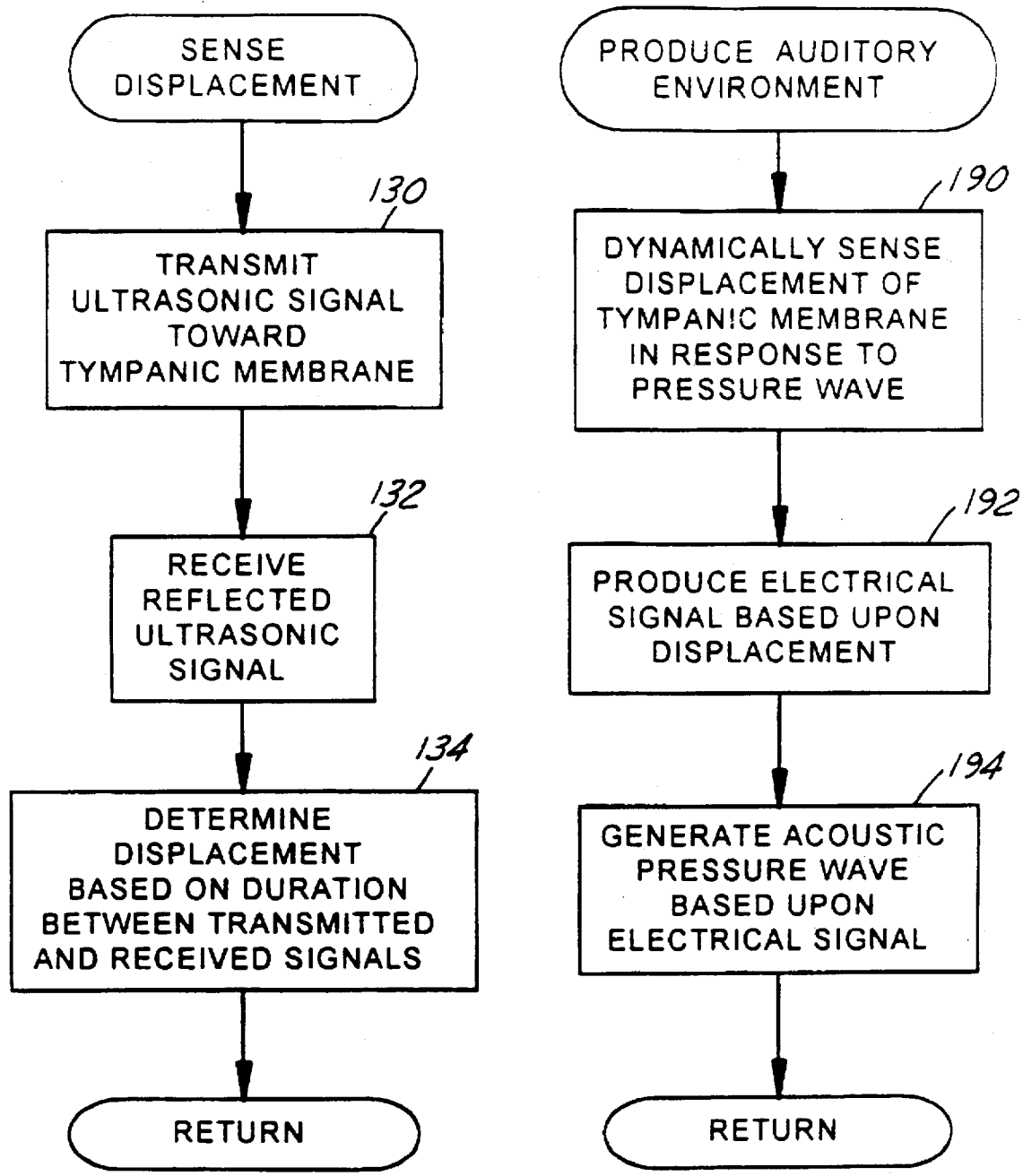

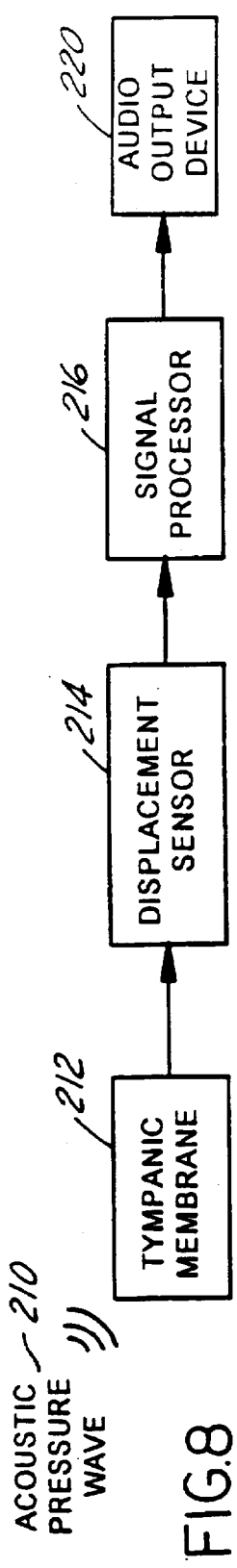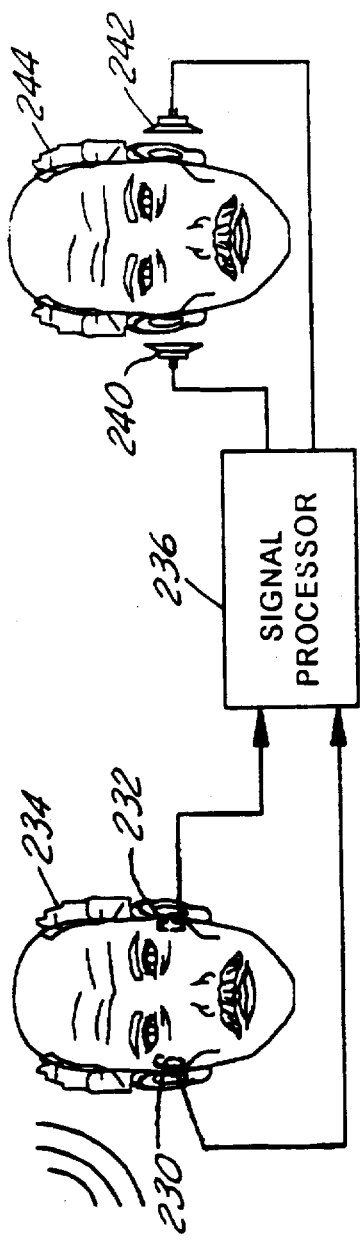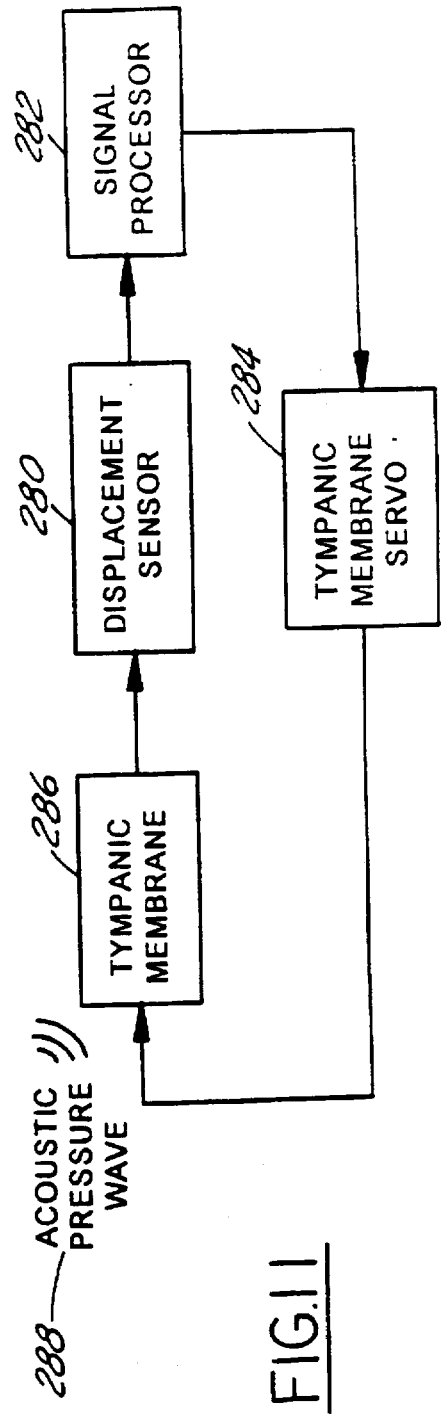

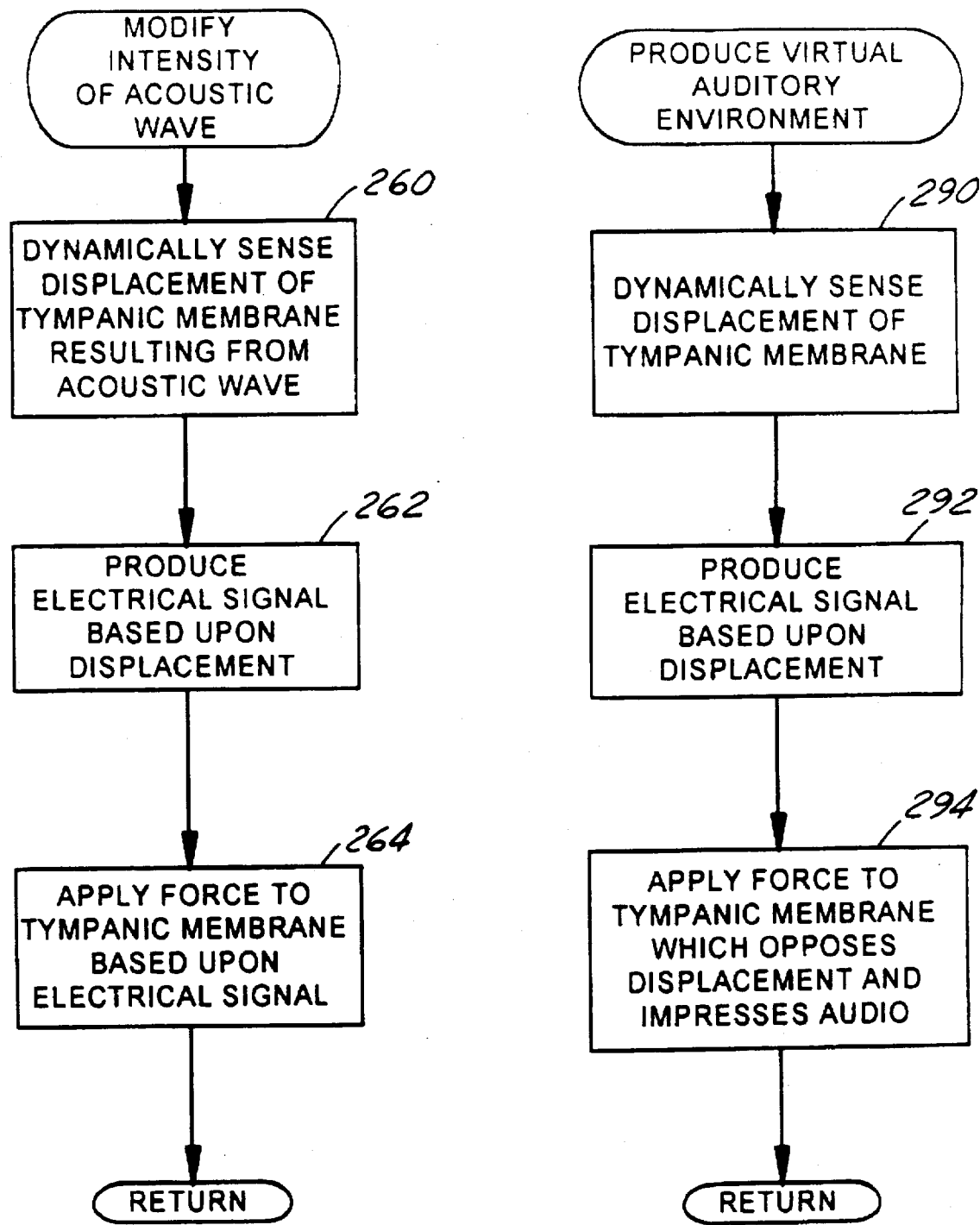

WEARABLE APPARATUS FOR MEASURING DISPLACEMENT OF AN IN VIVO TYMPANUM AND METHODS AND SYSTEMS FOR USE THEREWITH

TECHNICAL FIELD

The present invention relates to methods and systems for sensing an auditory environment, methods and systems for modifying a sensed auditory environment, and methods and systems for producing a virtual auditory environment.

BACKGROUND OF THE INVENTION

The spatio-temporal intensity of an acoustic pressure wave as sensed by an organism's ear is modulated and filtered by the physical configuration of that individual organism. In the case of humans, the physical configuration includes the configuration of the torso, the head, the pinna, and the auditory canal. The resulting modulation and filtering of the acoustic pressure wave can be described mathematically by a head related transfer function (HRTF). For each human, two head related transfer functions, one for each of two ears, can be defined.

It is known in the art that wave propagation in the auditory canal is substantially one-dimensional. Hence, an individual extracts three-dimensional spatial information of a sensed sound field based upon the diffraction of the sound and any corresponding spectral information induced by the individual's physical configuration. The three-dimensional spatial information is inferred by sensing and cognitive operations performed by the individual. By determining the two head related transfer functions for the individual, a single-channel audio source can be processed for application to headphones, or the like, to create a virtual sound source in a given direction of the individual's auditory space.

A current method of determining the head related transfer function is based upon measuring the sound pressure in each of the ears of the individual in response to a predetermined audio source. The sound pressure is also measured in response to the predetermined audio source with the individual absent. As a result, the influence of the auditory canal is not included in this method. Also, the modulation and filtering induced by the dynamic response of the tympanic membrane is not included.

SUMMARY OF THE INVENTION

It is an object of the present invention to measure an acoustic pressure wave as sensed by the tympanic membrane of an individual.

Another object of the present invention is to measure the modulation of an acoustic pressure wave caused by the physical configuration of an individual.

In carrying out the above objects, the present invention provides a method of electronically sensing an ambient acoustic pressure wave. The method comprises a step of dynamically sensing a displacement of a tympanic membrane of an individual in response to the acoustic pressure wave. The method also includes a step of producing an electrical signal in dependence upon the sensed displacement.

Further in carrying out the above objects, the present invention provides a method of modifying the intensity of an ambient acoustic pressure wave sensed by an individual. The method includes a step of dynamically sensing a displacement of a tympanic membrane of the individual, wherein the displacement results from the acoustic pressure wave. The method also includes a step of producing an electrical signal in dependence upon the sensed displacement. The method further includes a step of applying a force to the tympanic membrane in dependence upon the electrical signal.

Still further in carrying out the above objects, the present invention provides a method of producing a virtual auditory environment for an individual based upon a first electrical signal representative of audio. The method includes a step of dynamically sensing a displacement of a tympanic membrane of the individual, wherein the displacement results from an ambient acoustic pressure wave. The method also includes a step of producing a second electrical signal in dependence upon the sensed displacement. The method further includes a step of applying a force to the tympanic membrane in dependence upon the first electrical signal and the second electrical signal, wherein the force acts to attenuate the ambient acoustic pressure wave by opposing the displacement of the tympanic membrane resulting from the ambient acoustic pressure wave, and wherein the force acts to impress the audio onto the tympanic membrane by displacing the tympanic membrane in dependence upon the first electrical signal.

Yet still further in carrying out the above objects, the present invention provides systems which perform the steps of the above-described methods.

These and other features, aspects, and advantages of the present invention will become better understood with regard to the following description, appended claims, and accompanying drawings.

BRIEF DESCRIPTION OF THE DRAWINGS

FIG. 1 is a flow chart of an embodiment of a method of sensing an auditory environment in accordance with the present invention;

FIG. 2 is a flow chart of an embodiment of a method of sensing the displacement of a tympanic membrane;

FIG. 3 is a flow chart of another embodiment of a method of sensing the displacement of a tympanic membrane;

FIG. 7 is a flow chart of an embodiment of a method of producing an auditory environment;

FIG. 8 is a block diagram of an embodiment of a system for producing an auditory environment;

FIG. 9 is a schematic illustration of another embodiment of a system for producing an auditory environment;

FIG. 10 is a flow chart of an embodiment of a method of modifying the sensed intensity of an acoustic pressure wave;

FIG. 11 is a block diagram of an embodiment of a system for modifying the sensed intensity of an acoustic pressure wave;

FIG. 12 is a flow chart of an embodiment of a method for producing a virtual auditory environment;

BEST MODE FOR CARRYING OUT THE INVENTION

Figure 4:
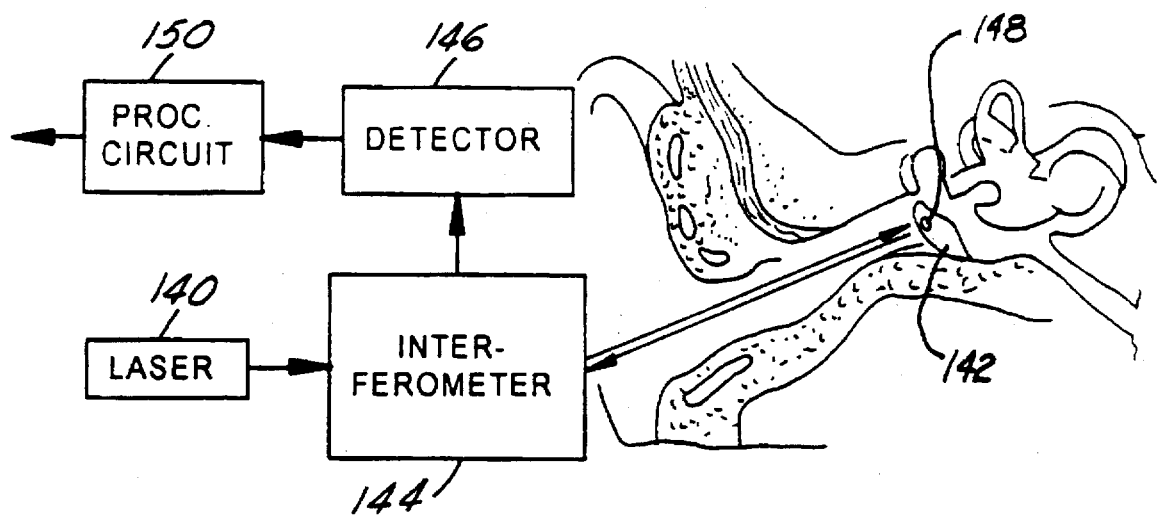
FIG. 4 is an illustration of an embodiment of a system for sensing the displacement of a tympanic membrane.

In accordance with the present invention, a displacement sensor, which is preferably highly damped, is used to dynamically detect the displacement of an organic eardrum as it is excited by an acoustic stimulus. The dynamic signal derived from the sensor represents the vibration of the eardrum and mirrors the acoustic pressure waves displacing it distorted only by the mechanical limitations of the eardrum system and any feedback actively imparted to it.

FIG. 1 is a flow chart of an embodiment of a method of sensing an auditory environment in accordance with the present invention. The auditory environment is comprised of at least one acoustic pressure wave which is typically an ambient pressure wave. Further, an individual is located within the auditory environment which is to be sensed. The method comprises a step of dynamically sensing a displacement of a tympanic membrane of the individual in response to excitation induced by the auditory environment, as indicated by block 100. The terms tympanic membrane, eardrum, and tympanum can be used interchangeably to refer to the flexible membrane or equivalent that serve in an organic ear to sense acoustic pressure waves.

The method further comprises a step of filtering the low frequency displacement components, as indicated by block 101. Thereafter, an electrical signal is produced in dependence upon the sensed displacement, as indicated by block 102. The electrical signal is representative of the vibration of the tympanic membrane, and hence, mirrors the acoustic pressure wave causing the displacement. Consequently, the method produces an electrical signal representative of the auditory environment as sensed by the individual.

FIG. 2 is a flow chart of an embodiment of a method of sensing the displacement of a tympanic membrane. The method includes a step of directing a laser beam toward the tympanic membrane, as indicated by block 110. The method further comprises a step of receiving a reflected light signal, wherein the reflected light signal includes a reflection of the laser beam from the tympanic membrane, as indicated by block 112. Optionally, the method may include a step of affixing a reflective member to the tympanic membrane in order to reflect the laser beam. As indicated by block 114, the method includes a step of using laser interferometry to sense the displacement of the tympanic membrane based upon an interference pattern formed by the laser beam and the reflected light signal.

FIG. 3 is a flow chart of another embodiment of a method of sensing the displacement of a tympanic membrane. The method includes a step of transmitting a first ultrasonic signal toward the tympanic membrane, as indicated by block 130. Preferably, the first ultrasonic signal is at a high frequency, such as 1 MHz or greater, and at a low power. The method further includes a step of receiving a second ultrasonic signal resulting from the first ultrasonic signal reflecting off of the tympanic membrane, as indicated by block 132. As indicated by block 134, the method determines the displacement based upon a time duration between transmitting the first ultrasonic signal and receiving the second ultrasonic signal. Preferably, the first ultrasonic signal is transmitted exterior to an auditory canal associated with the tympanic membrane, whereby the displacement of the tympanic membrane is measured with respect to a position outside the auditory canal.

FIG. 4 is an illustration of an embodiment of a system for sensing the displacement of a tympanic membrane. The system includes a laser 140 capable of directing a laser beam toward the tympanic membrane 142. The system further includes a laser interferometer 144 capable of producing an interference pattern in dependence upon the laser beam and a reflection of the laser beam off of the tympanic membrane 142. Preferably, a reflective member 146 is affixed to the surface of the tympanic membrane 142 in a non-injurious manner, such as using natural wax in the ear. The reflective member 146, which preferably includes a reflective gold disk, is employed to reflect the laser beam to the laser interferometer 144. Further, the system includes a detector 146 capable of sensing the interference pattern produced by the laser interferometer 148, and producing a detected signal representative thereof. A processing circuit 150 processes the detected signal to form a signal representative of the displacement of the tympanic membrane.

A fiber-optic interferometer which could be utilized with the present invention has been developed by NASA, Langley Research Center, and is disclosed in LASER Tech Briefs, at 45–46 (Fall, 1994), the disclosure of which is herein incorporated by reference. The NASA interferometer includes input and output optical fibers fused together at one end which is cleaved and polished. Infrared light from a laser diode enters along the input fiber and the reflected light travels along the output fiber toward a photo detector and signal-processing circuitry.

Figure 5:
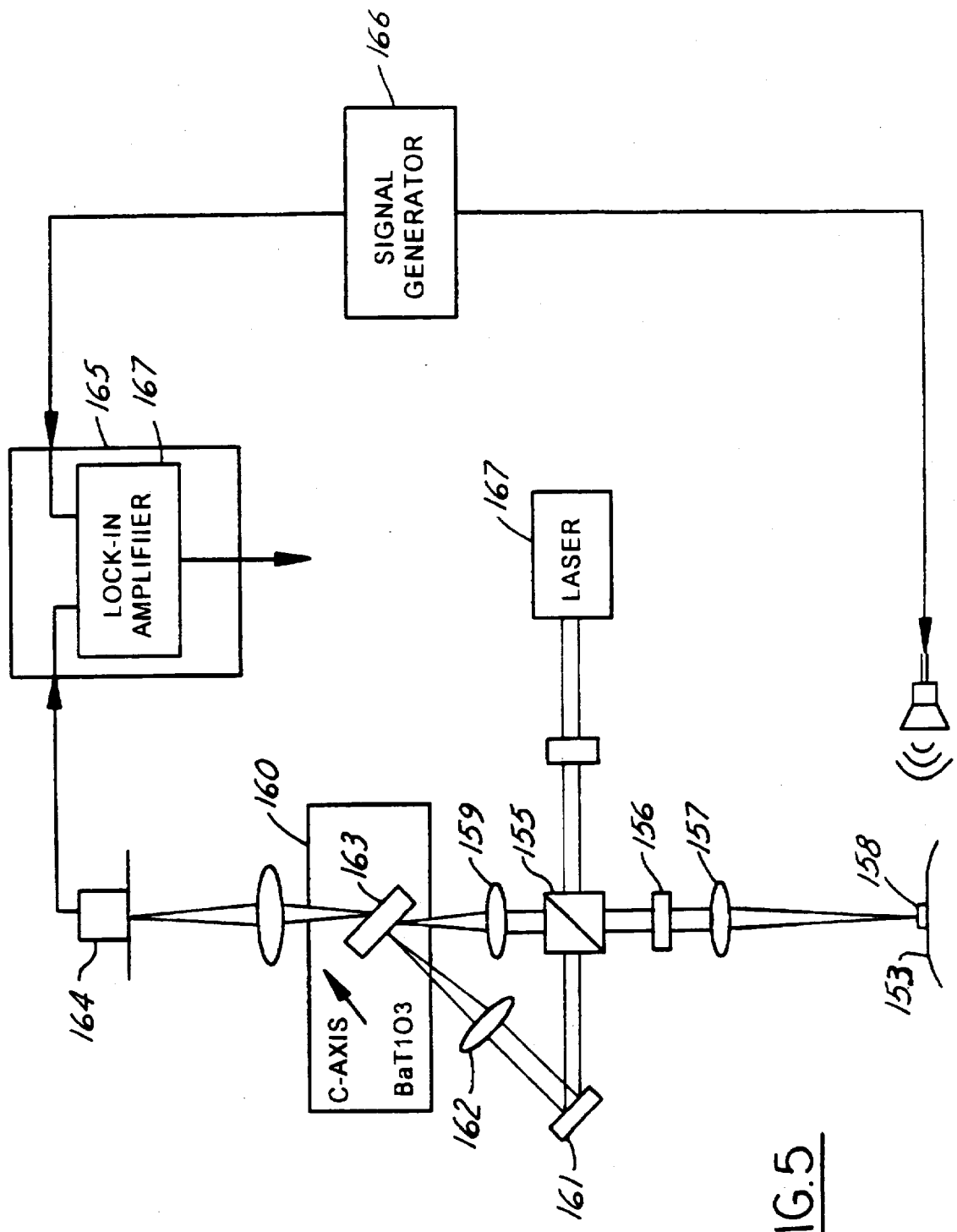
FIG. 5 is a schematic, block diagram of an embodiment of a system for sensing the displacement of the tympanic membrane.

FIG. 5 is a block diagram of another laser-based system for sensing the displacement of the tympanic membrane. The system comprises a laser 152 capable of producing a coherent reference beam. A first portion of the coherent reference beam is directed toward a tympanic membrane 153 by a combination comprising a half-wave plate 154, a polarizing beam splitter 155, a quarter-wave plate 156, and a first lens 157. A reflected beam results from the coherent beam reflecting off of a reflective member 158 affixed to the surface of the tympanic membrane. The reflected beam travels through the first lens 157, the quarter-wave plate 156, the polarizing beam splitter 155, and a second lens 159 for application to an optical filter 160.

A second portion of the coherent reference beam produced by the laser 152 is directed toward the optical filter 160 by a combination comprising the polarizing beam splitter 155, a mirror 161, and a third lens 162.

The second portion of the coherent reference beam combines with the reflected beam to produce an interference pattern. The optical filter 160 separates the interference pattern from the reference beam to facilitate observation of relatively weak interference patterns. The optical filter 160 may include a photo-refractive crystal 163, such as $BaTiO_3$.

The intensity of the interference pattern is read by a photodiode 164 which acts as a detector. The photodiode 164 produces a detected signal dependent upon the interference pattern. A processing circuit 165 processes the detected signal to form a signal representative of the displacement of the tympanic membrane.

Optionally, if the tympanic membrane is driven by a signal generator 166, the processing circuit can include a lock-in amplifier 167 which uses the second harmonic of the driving signal to detect a vibration amplitude and an acoustic phase shift of the tympanic membrane.

Figure 6:
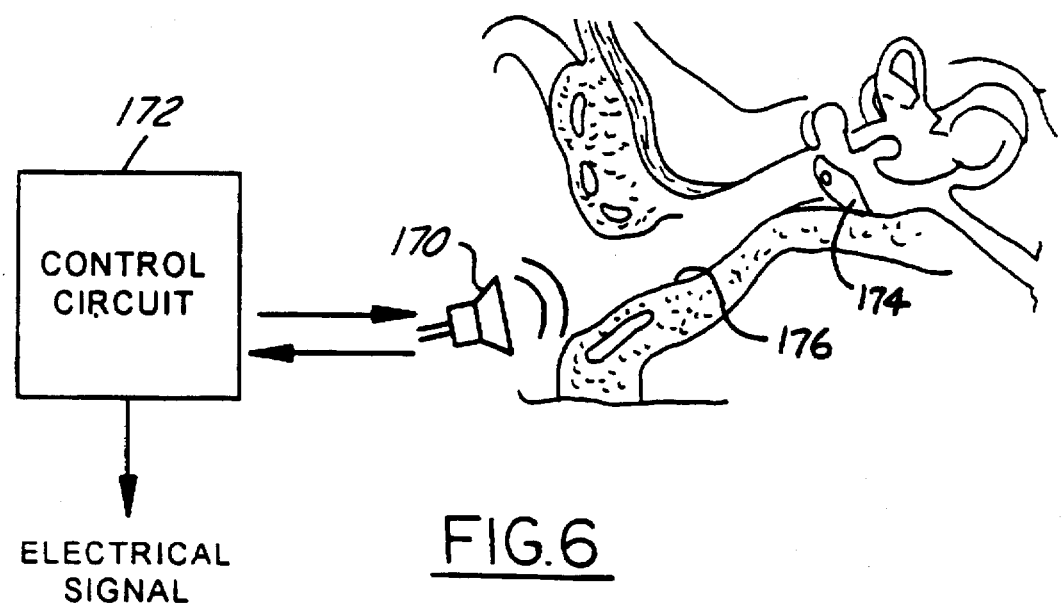
FIG. 6 is an illustration of another embodiment of a system for sensing the displacement of a tympanic membrane.

FIG. 6 is an illustration of another embodiment of a system for sensing the displacement of a tympanic membrane. The system includes an ultrasonic transducer 170 and a control circuit 172. The ultrasonic transducer 170 is capable of transmitting a first ultrasonic signal toward the tympanic membrane 174, and is further capable of receiving a second ultrasonic signal which reflects off of the tympanic membrane. Preferably, the first ultrasonic signal is at a high frequency, such as 1 MHz or greater, and at a low power.

The control circuit 172 is coupled to the ultrasonic transducer 170. The control circuit 172 commands the transmitting of the first ultrasonic signal. Further, the control circuit produces an electrical signal based upon a time duration between transmitting the first ultrasonic signal and receiving the second ultrasonic signal. Preferably, the ultrasonic transducer is located exterior to an auditory canal 176 associated with the tympanic membrane 174. Optionally, the system can include a filter which filters the electrical signal to attenuate at least one component of the displacement due to motion of the ultrasonic transducer 170.

Many different forms of displacement sensors can be used in accordance with the present invention. The intensity of a laser could also be utilized.

Regardless of the type of system employed for sensing the displacement of the tympanic membrane, it is preferred that the sensor is mounted to the individual using a highly damped support. The highly damped support aids in maintaining a fixed position of the sensor with respect to an unexcited position of the tympanic membrane. Preferably, the support maintains the position of the sensor from changing more rapidly than 15 Hz so that meaningful displacement measurements above 20 Hz can be extracted using digital filtering. More preferably, the support is contained within a wearable apparatus, which can be of any type conventionally known in the hearing aid or audio fields.

FIG. 7 is a flow chart of an embodiment of a method of producing an auditory environment. Specifically, the auditory environment is based upon at least one acoustic pressure wave as sensed by a first individual. As indicated by block 190, the method includes a step of dynamically sensing a displacement of a tympanic membrane of the first individual in response to the acoustic pressure wave. The acoustic pressure wave is typically an ambient pressure wave. Further, the acoustic pressure wave may contain a wave generated by the first individual, such as a vocally-produced sound.

The method further includes a step of producing an electrical signal in dependence upon the sensed displacement, as indicated by block 192. Optionally, the method could include a step of filtering the electrical signal to attenuate at least one component of the displacement due to motion of the first individual or a displacement sensor. As a further option, the method can include a step of processing the electrical signal in dependence upon an inverse head-related transfer function of the first individual.

As indicated by block 194, the method further includes a step of generating an acoustic pressure wave in dependence upon the electrical signal. As a result, the generated acoustic pressure wave forms the auditory environment as sensed by the first individual. If the generated acoustic pressure wave is generated in audio proximity to a second individual, the method can further include a step of processing the electrical signal based upon a head-related transfer function of the second individual.

FIG. 8 is a block diagram of an embodiment of a system for producing an auditory environment. Specifically, the auditory environment is based upon at least one acoustic pressure wave 210 as sensed by a tympanic membrane 212 of a first individual. The system includes a displacement sensor 214 which dynamically senses a displacement of the tympanic membrane of the first individual in response to the acoustic pressure wave 210. As described earlier, the displacement sensor 214 can include a laser-based system capable of directing a laser beam toward the tympanic membrane 212, receiving a reflected light signal which includes a reflection of the laser beam from the tympanic membrane 212, and sensing the displacement of the tympanic membrane 212 based upon an interference pattern formed by the laser beam and the reflected light signal. Alternatively the displacement sensor 214 can include an ultrasonic transducer and a control circuit as described earlier. Regardless of the type of displacement sensor employed, the displacement sensor 214 produces an electrical signal based upon sensed displacement of the tympanic membrane 212.

The displacement sensor 214 is coupled to a signal processor 216. The signal processor 216 processes the electrical signal to form a processed electrical signal. As an option, the signal processor 216 can form the processed signal based upon an inverse head-related transfer function of the first individual.

The signal processor 216 is coupled to an audio output device 220. The audio output device 220 produces an acoustic pressure wave based upon the processed electrical signal. As a result, the auditory environment sensed by the first individual is reproduced by the acoustic pressure wave generated by the audio output device 220. Typically, the audio output device 220 is located in proximity to a second individual so that the produced acoustic pressure wave is in audio proximity to the second individual. If the head-related transfer function of the second individual is known, the signal processor 216 can optionally form the processed electrical signal in dependence thereupon.

FIG. 9 is a schematic illustration of another embodiment of the system for producing an auditory environment. The system includes two displacement sensors 230 and 232, one for each of the two tympanic membranes of a first individual 234. The displacement sensors 230 and 232 dynamically sense the displacement of the corresponding tympanic membrane in response to the auditory environment sensed by the first individual 234. Electrical signals produced by the displacement sensors 230 and 232 are applied to a signal processor 236. The signal processor 236 forms two processed signals based upon the two electrical signals applied thereto.

Each of the two processed signals is applied to a corresponding one of two audio output devices 240 and 242. The audio output device 240 is located in audio proximity to one ear of a second individual 244, and the audio output device 242 is located in audio proximity to the other ear of the second individual 244. As a result, the second individual 244 can experience the auditory environment as sensed by the first individual 234.

Optionally, the signal processor can form the processed signals based upon two inverse head-related transfer functions, one for each ear, of the first individual 234, and two head-related transfer functions, one for each ear, of the second individual 244. In this version, the second individual 244 is capable of experiencing the auditory environment as if he were located in the auditory environment.

FIG. 10 is a flow chart of an embodiment of a method of modifying the sensed intensity of an acoustic pressure wave. As indicated by block 260, the method includes a step of dynamically sensing a displacement of a tympanic membrane of an individual, wherein the displacement results from the acoustic pressure wave. The method further includes a step of producing an electrical signal in dependence upon the sensed displacement, as indicated by block 262. Based upon the electrical signal, the method includes a step of applying a force to the tympanic membrane as indicated by block 264. By applying a force which acts to oppose the displacement of the tympanic membrane resulting from the acoustic pressure wave, the method acts to attenuate the intensity of the acoustic pressure wave sensed by the individual. Alternatively, by applying a force which acts to enhance the displacement of the tympanic membrane resulting from the acoustic pressure wave, the method amplifies the intensity of the acoustic pressure wave.

FIG. 11 is a block diagram of an embodiment of a system for modifying the intensity of an ambient acoustic pressure wave 288 as sensed by an individual. The system is comprised of a displacement sensor 280, a signal processor 282, and a servo 284. The displacement sensor 280 dynamically senses a displacement of a tympanic membrane 286 of the individual in response to the ambient acoustic pressure wave 288. The displacement sensor 280 produces an electrical signal in dependence upon the sensed displacement. The signal processor 282, which is coupled to the displacement sensor 280, processes the electrical signal to form a processed electrical signal. The signal processor 282 may include a filter which filters the electrical signal to attenuate at least one component of the displacement due to motion of the displacement sensor 280.

The servo 284 applies a force to the tympanic membrane 286 based upon the processed electrical signal produced by the signal processor 282. In one embodiment, the force produced by the servo 284 acts to oppose the displacement of the tympanic membrane resulting from the ambient acoustic pressure wave. In this embodiment, the system acts to attenuate the sensing of the ambient acoustic pressure wave by the individual. In another embodiment, the force applied by the servo 284 acts to enhance the displacement of the tympanic membrane resulting from the ambient acoustic pressure wave. In this embodiment, the system acts to amplify the sensing of the ambient acoustic pressure wave by the individual. Optionally, the signal processor 282 can include a filter having a transfer function such that selected components of the ambient acoustic pressure wave are amplified, and other selected components are attenuated.

FIG. 12 is a flow chart of an embodiment of a method of producing a virtual auditory environment for an individual, wherein the virtual auditory environment is based upon an electrical audio signal. More specifically, the electrical audio signal is either an analog or a digital signal representative of desired sound for the virtual auditory environment. The method includes a step of dynamically sensing a displacement of a tympanic membrane of the individual, as indicated by block 290. The displacement of the tympanic membrane partially results from an ambient acoustic pressure wave which strikes the tympanic membrane.

The method further includes a step of producing a second electrical signal in dependence upon the sensed displacement, as indicated by block 292.

As indicated by block 294, the method further includes a step of applying a force to the tympanic membrane in dependence upon the first electrical signal and the second electrical signal. The applied force acts to attenuate the ambient acoustic pressure wave by opposing the displacement of the tympanic membrane resulting from the ambient acoustic pressure wave. Further, the applied force acts to impress the audio represented by the first electrical signal onto the tympanic membrane by displacing the tympanic membrane in dependence thereupon.

Figure 13:
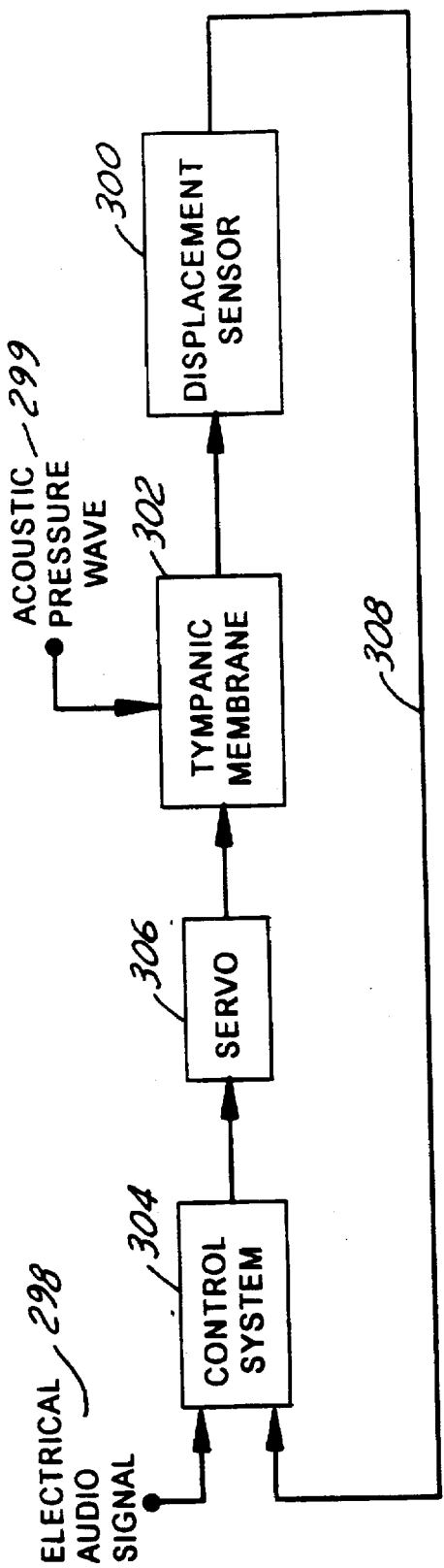
FIG. 13 is a block diagram of an embodiment of a system for producing a virtual auditory environment.

FIG. 13 is a block diagram of an embodiment of a system for producing a virtual auditory environment for an individual, wherein the virtual auditory environment is based upon an electrical audio signal 298. More specifically, the electrical audio signal is either an analog or a digital signal representative of desired sound for the virtual auditory environment. A displacement sensor 300 dynamically senses a displacement of a tympanic membrane 302 of the individual. The displacement of the tympanic membrane 302 partially results from an ambient acoustic pressure wave 299 striking the tympanic membrane 302. The displacement sensor 300 produces an electrical signal 308 based upon the sensed displacement.

The displacement sensor 300 is coupled to a control system 304. The control system 304 produces a control signal based upon the electrical audio signal 298 and based upon the electrical signal 308 from the displacement sensor 300. Typically, the control system 304 produces the control signal based upon a difference between the electrical audio signal 298 and the electrical signal 308.

The control system 304 can have a digital implementation using a microprocessor and a memory, wherein the microprocessor performs a sequence of programmed steps. Alternatively, the control system 304 can have an analog implementation using standard means for performing analog computations.

The control system 304 is coupled to a servo 306. The servo 306 applies a force to the tympanic membrane 302 based upon the control signal from the control system 304. The force applied by the servo acts to attenuate the ambient acoustic pressure wave 299 by opposing the displacement of the tympanic membrane resulting from the ambient acoustic pressure wave. Further, the force acts to impress the audio onto the tympanic membrane 302 by displacing the tympanic membrane 302 based upon the electrical audio signal 298.

Figure 14:
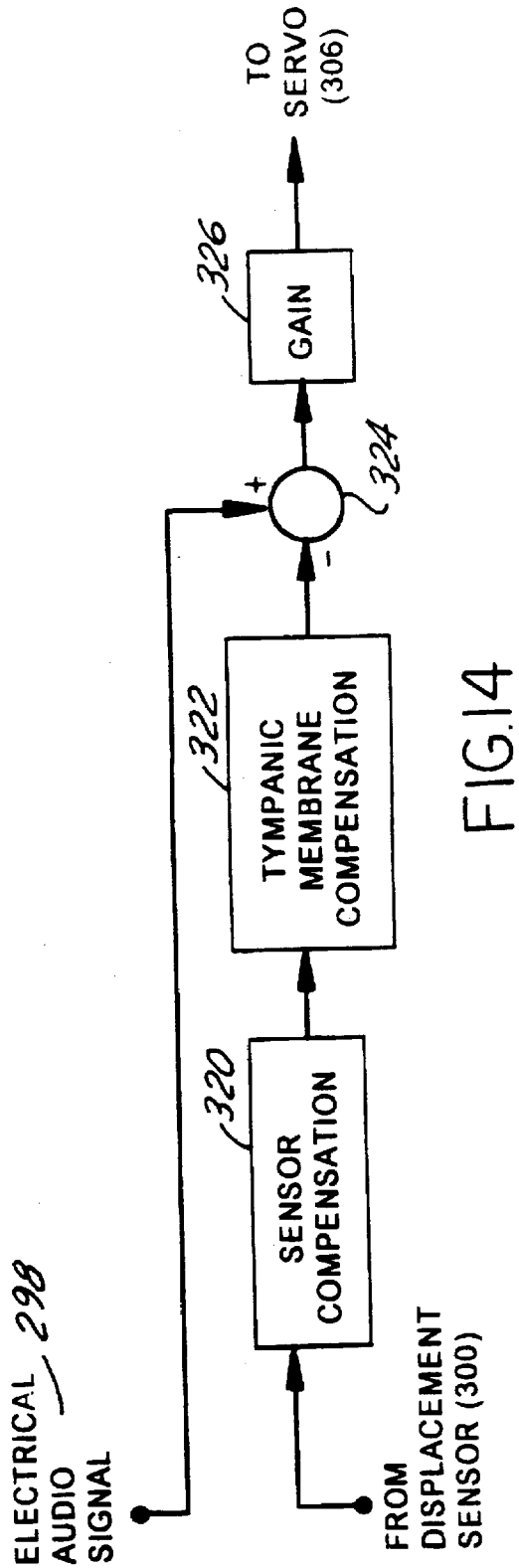
FIG. 14 is a block diagram of an embodiment of a control system in accordance with embodiments of the present invention.

FIG. 14 is a block diagram of an embodiment of a control system in accordance with embodiments of the present invention. The signal from the displacement sensor 300 is applied to a sensor compensator 320. The sensor compensator 320 compensates for the electrical and mechanical dynamic response of the displacement sensor 300. Preferably, the sensor compensator 320 includes an inverse transfer function model of the displacement sensor 300.

The output of the sensor compensator 320 is applied to a tympanic membrane compensator 322. The tympanic membrane compensator 322 compensates for the mechanical dynamic response of the tympanic membrane 302 which is exhibited when an acoustic pressure wave is encountered. Preferably, the tympanic membrane compensator 322 includes an inverse transfer function model of the tympanic membrane 302.

A differencing element 324 forms a difference quantity between the electrical audio signal 298 and the compensated displacement sensor signal. The output of the differencing element 324 is applied to an amplifier 326. The output of the amplifier 326 is then applied to the servo 306.

In a digital implementation of the control system 304, the sensor compensator 320, the tympanic membrane compensator 322, and the differencing element 324 are embodied by a microprocessor which performs the compensation and differencing steps. Alternatively, analog circuits can be employed to provide inverse models of the displacement sensor 300 and the tympanic membrane, and a differencing element.

The present invention provides a method and system for instrumentally sensing an acoustic pressure wave that has been subject to physical modulation precisely as it is sensed by an organic eardrum. The invention utilizes a wearable apparatus that physically measures the actual dynamic displacement of that eardrum.

The above-described embodiments of the present invention have many advantages. By sensing the displacement of the tympanic membrane in response to an acoustic pressure wave, it is possible to easily derive the head related transfer function for an individual by non-intrusively capturing an encoded sound pressure signal. The system dynamically senses the HRTF.

Further, embodiments of the present invention allow the capturing of a dynamically-changing acoustic pressure wave which has been individually encoded in a form that enables the individual to infer the spatiality of the sound field. Moreover, it is not required to have any prior knowledge of particular characteristics of the individual.

Embodiments of the present invention also make it possible to sense a vocal sound generated by an individual and conveyed by bone and other tissue to the tympanic membrane for the purpose of determining an internally-sensed form of the vocal sound. This enables the recording of speech of an individual as it is sensed by the individual.

By directly sensing activity of the tympanic membrane, feedback can be provided for closed loop applications such as noise cancellation. Similarly, an auditory signal intensification function comparable to image intensification for vision can be performed.

The present invention can be used as a microphone that captures the acoustic signal as it has been mechanically processed by the physical structure of the head, body and ear. This makes possible the extraction of directional information from the acoustic signal.

The present invention also allows the creation of synthesized sounds with artificially imposed spatial characteristics. This can be used to measure the mechanical processing done by the head, body and ear transforms. The invention further provides a method and system for sensing eardrum activity for closed loop applications like noise cancellation, audio intensification and signal improvement.

It should be noted that the present invention may be used in a wide variety of different constructions encompassing many alternatives, modifications, and variations which are apparent to those with ordinary skill in the art. Accordingly, the present invention is intended to embrace all such alternatives, modifications, and variations as fall within the spirit and broad scope of the appended claims.

What is claimed is:

1. A method of producing an auditory environment based upon a first acoustic pressure wave sensed by a first individual, the method comprising the steps of:

dynamically sensing a displacement of a tympanic membrane of the first individual in response to the first acoustic pressure wave;

producing an electrical signal in dependence upon the sensed displacement; and generating a second acoustic pressure wave in dependence upon the electrical signal, wherein the auditory environment is based upon the second acoustic pressure wave.

2. The method of claim 1 wherein the step of dynamically sensing the displacement includes the steps of:

directing a laser beam toward the tympanic membrane;

receiving a reflected light signal, wherein the reflected light signal includes a reflection of the laser beam off of the tympanic membrane; and using laser interferometry to sense the displacement of the tympanic membrane based upon an interference pattern formed by the laser beam and the reflected light signal.

3. The method of claim 2 further comprising the step of affixing a reflective member to the tympanic membrane which reflects the laser beam.

4. The method of claim 1 wherein the step of dynamically sensing the displacement comprises use of a laser.

5. The method of claim 1 wherein the step of dynamically sensing the displacement includes the steps of:

transmitting a first ultrasonic signal toward the tympanic membrane;

receiving a second ultrasonic signal resulting from the first ultrasonic signal reflecting off the tympanic membrane; and determining the displacement based upon a time duration between transmitting the first ultrasonic signal and receiving the second ultrasonic signal.

6. The method of claim 5 wherein the first ultrasonic signal is transmitted exterior to an auditory canal associated with the tympanic membrane.

7. The method of claim 1 further comprising the step of filtering the electrical signal to attenuate at least one component of the displacement due to motion of the first individual.

8. The method of claim 1 wherein the first acoustic pressure wave is an ambient pressure wave.

9. The method of claim 1 wherein the first acoustic pressure wave is generated by the first individual.

10. The method of claim 1 further comprising the step of processing the electrical signal in dependence upon an inverse head related transfer function of the first individual.

11. A method of producing an auditory environment based upon a first acoustic pressure wave sensed by a first individual, the method comprising the steps of:

dynamically sensing a displacement of a tympanic membrane of the first individual in response to the first acoustic pressure wave;

producing an electrical signal in dependence upon the sensed displacement; and generating a second acoustic pressure wave in dependence upon the electrical signal, wherein the auditory environment is based upon the second acoustic pressure wave, wherein the second acoustic pressure wave is generated in audio proximity to a second individual.

12. A method of producing an auditory environment based upon a first acoustic pressure wave sensed by a first individual, the method comprising the steps of:

dynamically sensing a displacement of a tympanic membrane of the first individual in response to the first acoustic pressure wave;

producing an electrical signal in dependence upon the sensed displacement;

generating a second acoustic pressure wave in dependence upon the electrical signal, wherein the auditory environment is based upon the second acoustic pressure wave; and processing the electrical signal in dependence upon a head related transfer function of a second individual.

13. A system for producing an auditory environment based upon a first acoustic pressure wave sensed by a first individual, the system comprising:

a displacement sensor which dynamically senses a displacement of a tympanic membrane of the first individual in response to the first acoustic pressure wave, the displacement sensor producing an electrical signal in dependence upon the sensed displacement;

a signal processor, coupled to the displacement sensor, which processes the electrical signal to form a processed electrical signal; and an audio output device, coupled to the signal processor, which produces a second acoustic pressure wave based upon the processed electrical signal, wherein the auditory environment is based upon the second acoustic pressure wave.

14. The system of claim 13 wherein the displacement sensor includes:

a laser which produces a coherent beam directed toward the tympanic membrane;

a laser interferometer which receives the coherent beam and a reflected beam from the tympanic membrane, and produces an interference pattern based thereupon;

a detector which produces a detected signal based upon the interference pattern; and a processing circuit which forms the electrical signal representative of displacement from the detected signal.

15. The system of claim 14 further comprising a reflective member affixed to the tympanic membrane, which reflects the coherent beam.

16. The system of claim 15 wherein the reflective member includes a reflective gold disc.

17. The system of claim 13 wherein said displacement sensor comprises a laser.

18. The system of claim 13 wherein the displacement sensor includes:

an ultrasonic transducer capable of transmitting a first ultrasonic signal toward the tympanic membrane and receiving a second ultrasonic signal which reflects off the tympanic membrane; and a control circuit, coupled to the ultrasonic transducer, which commands the transmitting of the first ultrasonic signal and produces the electrical signal in dependence upon a time duration between transmitting the first ultrasonic signal and receiving the second ultrasonic signal.

19. The system of claim 18 wherein the ultrasonic transducer is located exterior to an auditory canal associated with the tympanic membrane.

20. The system of claim 13 wherein the signal processor includes a filter which filters the electrical signal to attenuate at least one component of the displacement due to motion of the displacement sensor.

21. The system of claim 13 wherein the first acoustic pressure wave is an ambient pressure wave.

22. The system of claim 13 wherein the first acoustic pressure wave is generated by the first individual.

23. The system of claim 13 wherein the signal processor forms the processed signal in dependence upon an inverse head related transfer function of the first individual.

24. A system for producing an auditory environment based upon a first acoustic pressure wave sensed by a first individual, the system comprising:

a displacement sensor which dynamically senses a displacement of a tympanic membrane of the first individual in response to the first acoustic pressure wave, the displacement sensor producing an electrical signal in dependence upon the sensed displacement;

a signal processor, coupled to the displacement sensor, which processes the electrical signal to form a processed electrical signal; and an audio output device, coupled to the signal processor, which produces a second acoustic pressure wave based upon the processed electrical signal, wherein the auditory environment is based upon the second acoustic pressure wave, wherein the second acoustic pressure wave is generated in audio proximity to a second individual.

25. A system for producing an auditory environment based upon a first acoustic pressure wave sensed by a first individual, the system comprising:

a displacement sensor which dynamically senses a displacement of a tympanic membrane of the first individual in response to the first acoustic pressure wave, the displacement sensor producing an electrical signal in dependence upon the sensed displacement;

a signal processor, coupled to the displacement sensor, which processes the electrical signal to form a processed electrical signal in dependence upon a head related transfer function of a second individual; and an audio output device, coupled to the signal processor, which produces a second acoustic pressure wave based upon the processed electrical signal, wherein the auditory environment is based upon the second acoustic pressure wave.

26. A method of modifying the intensity of an ambient acoustic pressure wave sensed by an individual, the method comprising the steps of:

dynamically sensing a displacement of a tympanic membrane of the individual, wherein the displacement results from the acoustic pressure wave;

producing an electrical signal in dependence upon the sensed displacement; and applying a force to the tympanic membrane in dependence upon the electrical signal.

27. The method of claim 26 wherein the force acts to oppose the displacement of the tympanic membrane resulting from the acoustic pressure wave.

28. The method of claim 26 wherein the force acts to enhance the displacement of the tympanic membrane resulting from the acoustic pressure wave.

29. The method of claim 26 wherein the step of dynamically sensing the displacement includes the steps of:

directing a laser beam toward the tympanic membrane;

receiving a reflected light signal, wherein the reflected light signal includes a reflection of the laser beam off of the tympanic membrane; and using laser interferometry to sense the displacement of the tympanic membrane based upon an interference pattern formed by the laser beam and the reflected light signal.

30. The method of claim 29 further comprising the step of affixing a reflective member to the tympanic membrane which reflects the laser beam.

31. The method of claim 26 wherein the step of dynamically sensing the displacement comprises use of a laser.

32. The method of claim 26 wherein the step of dynamically sensing the displacement includes the steps of:

transmitting a first ultrasonic signal toward the tympanic membrane;

receiving a second ultrasonic signal resulting from the first ultrasonic signal reflecting off the tympanic membrane; and determining the displacement based upon a time duration between transmitting the first ultrasonic signal and receiving the second ultrasonic signal.

33. The method of claim 32 wherein the first ultrasonic signal is transmitted exterior to an auditory canal associated with the tympanic membrane.

34. The method of claim 26 further comprising the step of filtering the electrical signal to attenuate at least one component of the displacement due to motion of the first individual.

35. A system for modifying the intensity of an ambient acoustic pressure wave sensed by an individual, the system comprising:

a displacement sensor which dynamically senses a displacement of a tympanic membrane of the individual in response to the acoustic pressure wave, the displacement sensor producing an electrical signal in dependence upon the sensed displacement;

a signal processor, coupled the displacement sensor, which processes the electrical signal to form a processed electrical signal; and a servo which applies a force to the tympanic membrane in dependence upon the processed electrical signal.

36. The system of claim 35 wherein the force acts to oppose the displacement of the tympanic membrane resulting from the acoustic pressure wave.

37. The system of claim 35 wherein the force acts to enhance the displacement of the tympanic membrane resulting from the acoustic pressure wave.

38. The system of claim 35 wherein the displacement sensor includes:

a laser which produces a coherent beam directed toward the tympanic membrane;

a laser interferometer which receives the coherent beam and a reflected beam from the tympanic membrane, and produces an interference pattern based thereupon;

a detector which produces a detected signal based upon the interference pattern; and a processing circuit which forms the electrical signal representative of displacement from the detected signal.

39. The system of claim 38 further comprising a reflective member affixed to the tympanic membrane, which reflects the coherent beam.

40. The system of claim 39 wherein the reflective member includes a reflective gold disc.

41. The system of claim 35 wherein said displacement sensor comprises a laser.

42. The system of claim 35 wherein the displacement sensor includes:

an ultrasonic transducer capable of transmitting a first ultrasonic signal toward the tympanic membrane and receiving a second ultrasonic signal which reflects off the tympanic membrane; and a control circuit, coupled to the ultrasonic transducer, which commands the transmitting of the first ultrasonic signal and produces the electrical signal in dependence upon a time duration between transmitting the first ultrasonic signal and receiving the second ultrasonic signal.

43. The system of claim 42 wherein the ultrasonic transducer is located exterior to an auditory canal associated with the tympanic membrane.

44. The system of claim 35 wherein the signal processor includes a filter which filters the electrical signal to attenuate at least one component of the displacement due to motion of the displacement sensor.

45. A method of producing a virtual auditory environment for an individual, the virtual auditory environment based upon a first electrical signal representative of audio, the method comprising the steps of:

dynamically sensing a displacement of a tympanic membrane of the individual in response to an ambient acoustic pressure wave;

producing a second electrical signal in dependence upon the sensed displacement; and applying a force to the tympanic membrane in dependence upon the first electrical signal and the second electrical signal, wherein the force acts to attenuate the ambient acoustic pressure wave by opposing the displacement of the tympanic membrane resulting from the ambient acoustic pressure wave, and wherein the force acts to impress the audio onto the tympanic membrane by displacing the tympanic membrane in dependence upon the first electrical signal.

46. The method of claim 45 wherein the step of dynamically sensing the displacement includes the steps of:

directing a laser beam toward the tympanic membrane;

receiving a reflected light signal, wherein the reflected light signal includes a reflection of the laser beam off of the tympanic membrane; and using laser interferometry to sense the displacement of the tympanic membrane based upon an interference pattern formed by the laser beam and the reflected light signal.

47. The method of claim 46 further comprising the step of affixing a reflective member to the tympanic membrane which reflects the laser beam.

48. The method of claim 45 wherein said step of dynamically sensing a displacement comprises use of a laser.

49. The method of claim 45 wherein the step of dynamically sensing the displacement includes the steps of:

transmitting a first ultrasonic signal toward the tympanic membrane;

receiving a second ultrasonic signal resulting from the first ultrasonic signal reflecting off the tympanic membrane; and determining the displacement based upon a time duration between transmitting the first ultrasonic signal and receiving the second ultrasonic signal.

50. The method of claim 49 wherein the first ultrasonic signal is transmitted exterior to an auditory canal associated with the tympanic membrane.

51. The method of claim 45 further comprising the step of filtering the second electrical signal to attenuate at least one component of the displacement due to motion of the first individual.

52. A system for producing a virtual auditory environment for an individual, the virtual auditory environment based upon a first electrical signal representative of audio, the system comprising:

a displacement sensor which dynamically senses a displacement of a tympanic membrane of the individual in response to an ambient acoustic pressure wave, the displacement sensor producing a second electrical signal based upon the sensed displacement;

a control system which produces a third electrical signal based upon the first electrical signal and the second electrical signal; and a servo which applies a force to the tympanic membrane in dependence upon the third electrical signal;

wherein the force acts to attenuate the ambient acoustic pressure wave by opposing the displacement of the tympanic membrane resulting from the ambient acoustic pressure wave, and wherein the force acts to impress the audio onto the tympanic membrane by displacing the tympanic membrane in dependence upon the first electrical signal.

53. The system of claim 52 wherein the control system produces the third electrical signal based upon a difference between the first electrical signal and the second electrical signal.

54. The system of claim 52 wherein the displacement sensor includes:

a laser which produces a coherent beam directed toward the tympanic membrane;

a laser interferometer which receives the coherent beam and a reflected beam from the tympanic membrane, and produces an interference pattern based thereupon;

a detector which produces a detected signal based upon the interference pattern; and a processing circuit which forms the second electrical signal based upon the detected signal.

55. The system of claim 54 further comprising a reflective member affixed to the tympanic membrane, which reflects the coherent beam.

56. The system of claim 55 wherein the reflective member includes a reflective gold disk.

57. The system of claim 52 wherein said displacement sensor comprises a laser.

58. The system of claim 52 wherein the displacement sensor includes:

an ultrasonic transducer capable of transmitting a first ultrasonic signal toward the tympanic membrane and receiving a second ultrasonic signal which reflects off the tympanic membrane; and a control circuit, coupled to the ultrasonic transducer, which commands the transmitting of the first ultrasonic signal and produces the second electrical signal in dependence upon a time duration between transmitting the first ultrasonic signal and receiving the second ultrasonic signal.

59. The system of claim 58 wherein the ultrasonic transducer is located exterior to an auditory canal associated with the tympanic membrane.

60. The system of claim 52 further comprising a filter which filters the second electrical signal to attenuate at least one component of the displacement due to motion of the first displacement sensor.

61. A system for electronically sensing an ambient acoustic pressure wave, the system comprising:

a displacement sensor which dynamically senses a displacement of a tympanic membrane of an individual using an ultrasonic transducer capable of transmitting a first ultrasonic signal toward the tympanic membrane and receiving a second ultrasonic signal which reflects off the tympanic membrane; and a control circuit, coupled to the ultrasonic transducer, which commands the transmitting of the first ultrasonic signal and produces an electrical signal in dependence upon a time duration between transmitting the first ultrasonic signal and receiving the second ultrasonic signal.

62. The system of claim 61 wherein the ultrasonic transducer is located exterior to an auditory canal associated with the tympanic membrane.

63. A method of electronically sensing an ambient acoustic pressure wave by dynamically sensing displacement of a tympanic membrane of an individual in response to the ambient acoustic pressure wave, the method comprising:

transmitting a first ultrasonic signal toward the tympanic membrane;

receiving a second ultrasonic signal resulting from the first ultrasonic signal reflecting off the tympanic membrane;

determining the displacement based upon a time duration between transmitting the first ultrasonic signal and receiving the second ultrasonic signal; and producing an electrical signal based upon the sensed displacement.

64. The method of claim 63 wherein the first ultrasonic signal is transmitted exterior to an auditory canal associated with the tympanic membrane.

* * * * *